United States Patent [19]
Ishikawa et al.

[11] Patent Number: 6,007,810
[45] Date of Patent: Dec. 28, 1999

[54] CHONDROITINASE COMPOSITIONS

[75] Inventors: Shin-ichi Ishikawa; Mine Higuchi, both of Tokyo, Japan

[73] Assignee: Seikagaku Corporation, Tokyo, Japan

[21] Appl. No.: 09/070,763

[22] Filed: May 1, 1998

[30] Foreign Application Priority Data

May 2, 1997 [JP] Japan .................................... 9-127785

[51] Int. Cl.⁶ .......................... A61K 38/46; A61K 38/47; C12N 9/26
[52] U.S. Cl. .................................... 424/94.62; 424/94.61; 435/201
[58] Field of Search .............................. 424/94.62, 94.61; 435/200, 201, 202

[56] References Cited

U.S. PATENT DOCUMENTS

| | | | |
|---|---|---|---|
| 4,696,816 | 9/1987 | Brown | 424/94.65 |
| 5,496,718 | 3/1996 | Hashimoto et al. | 435/232 |
| 5,716,617 | 2/1998 | Khandke et al. | 424/94.62 |

FOREIGN PATENT DOCUMENTS

| | | |
|---|---|---|
| 0576294 | 12/1993 | European Pat. Off. . |
| 4330280 | 4/1991 | Japan . |
| 06098769 | 4/1994 | Japan . |
| 07067642 | 3/1995 | Japan . |
| 1067253 | 5/1967 | United Kingdom . |
| 9300807 | 1/1993 | WIPO . |

OTHER PUBLICATIONS

Kato, et al., Chemonucleolysis, No. 253, Apr. 1990, pp. 301–308.

*Primary Examiner*—Jon P. Weber

[57] ABSTRACT

This invention provides pharmaceutical compositions containing chondroitinase wherein a decrease in enzyme activity is very little even after long-term storage, and the pharmaceutical compositions are characterized in that they contain chondroitinase and a pharmaceutical carrier, and that an amount of reducing impurities per 1 g of said pharmaceutical carrier is 0.4 mL or less as a titer by a titration method with 0.01 N of ammonium ceric nitrate.

20 Claims, No Drawings

CHONDROITINASE COMPOSITIONS

This invention relates to pharmaceutical compositions containing chondroitinase, and to agents consisting of said pharmaceutical composition for the treatment of intervertebral disc herniation.

Chondroitinase ABC [EC 4.2.2.4] is an enzyme having an action that degrades glycosaminoglycan to unsaturated oligosaccharide and unsaturated disaccharide. It strongly catalyzes the degradation of chondroitin sulfate A derived from mammal cartilage, chondroitin sulfate C derived from shark cartilage and chondroitin sulfate B (dermatan sulfate) derived from mammal skin, and weakly catalyzes the degradation of hyaluronic acid.

For this enzyme, enzymes produced by bacteria such as *Proteus vulgaris* etc. are commercialized as research reagents for removing glycosaminoglycan from animal tissues and for identifying glycosaminoglycan in tissues.

On the other hand, the intervertebral disc dissolution method (ID therapy) was developed for the treatment of disc herniation which is identified as a cause of human lumbar pain. In this method, a protease derived from plant papaya, e.g. chymopapain, or a collagenase derived from bacteria, and the like is injected into the intervertebral disc of a patient with herniation to dissolve the nucleus pulposus. Chymopapain is commercially available as a pharmaceutical product (trade name, Chymodiactin$^R$) in Europe and the United States.

However, the ID therapy using the above-mentioned protease has drawbacks that it degrades not only the herniated disc between spine and intervertebral disc but also proteins in the surrounding structural tissue, and that it tends to cause side effects such as neuroparalysis, allergy and the like.

In recent years, attempts have been made to treat disc herniation by directly administering chondroitinase ABC or chondroitinase AC into the intervertebral disc, and the use as an agent for the treatment of disc herniation has been expected [see, U.S. Pat. No. 4,696,816, Clinical Orthopaedics, 253, 301–308 (1990)].

Compositions containing chondroitinase have been described, for example, in Japanese Laid-Open Patent Publication No. 330280/92, U.S. Pat. No. 5,496,718 and EP-A-576,294. For example, Japanese Laid-Open Patent Publication No. 330280/92 discloses dried and stabilized chondroitinase ABC containing at least one additive component selected from the group consisting of dextrans, sucrose, lactose, maltose, mannitol, xylitol, sorbitol, and serum albumin. Also, U.S. Pat. No. 5,496,718 and EP-A-576,294 describe purified chondroitinase ABC with extremely high purity and high stability, and pharmaceutical compositions containing thereof. Furthermore, WO 93/00807 discloses compositions consisting of biomaterial, polyethylene glycol and sugar (including sucrose), which are suitable to freeze and dry biomaterials (including enzymes), although it does not specifically describe chondroitinase.

Chondroitinase is an unstable substance, and has a problem that the enzyme activity decreases gradually at the time of formulation or during long-term storage, when formulated in the form of freeze-dried preparations, solution preparations and the like using a conventional pharmaceutical carrier, in accordance with a method as described in the above literatures.

The purpose of the present invention is to 35 develop pharmaceutical compositions containing chondroitinase, having very little decrease in the enzyme activity at the time of formulation or during long-term storage.

Through various investigation of factors causing the decrease in enzyme activity in a pharmaceutical composition which is prepared from chondroitinase and a pharmaceutical carrier, the inventors found that reducing impurities in a pharmaceutical carrier is mainly responsible for it, and have completed the present invention.

Thus, the present invention provides pharmaceutical compositions, characterized in that they contain chondroitinase and a pharmaceutical carrier, and that an amount of reducing impurities contained per 1 g of said pharmaceutical carrier is 0.4 mL or less as a titer by a titration method with 0.01 N ammonium ceric nitrate (hereinafter, "pharmaceutical compositions of the invention").

The invention also provides agents consisting of said pharmaceutical composition for the treatment of disc herniation, (hereinafter, also referred to as "agents of the invention").

DESCRIPTION OF THE EMBODIMENTS

Hereinbelow, pharmaceutical compositions and the agents of the invention will be described in more detail.

Chondroitinase:

Chondroitinase used in pharmaceutical compositions of the invention is not particularly limited, as far as an enzyme degrades chondroitin sulfate. More specifically, as chondroitinase, chondroitinase ABC (derived from *Proteus vulgaris*; U.S. Pat. No. 5,496,718, EP-A-576,294, T. Yamagata, H. Saito, O. Habuchi, S. Suzuki, J. Biol. Chem., 243, 1523 (1968), S. Suzuki, H. Saito, T. Yamagata, K. Anno, N. Seno, Y. Kawai, T. Furuhashi, J. Biol. Chem., 243, 1543 (1968)), chondroitinase AC (derived from *Flavobacterium heparinum*; T. Yamagata, H. Saito, O. Habuchi, S. Suzuki, J. Biol. Chem., 243, 1523 (1968)), chondroitinase AC II (derived from *Arthrobacter aurescens*; K. Hiyama, S. Okada, J. Biol. Chem., 250, 1824 (1975), K. Hiyama, S. Okada, J. Biochem. (Tokyo), 80, 1201 (1976)), chondroitinase AC III (derived from Flavobacterium sp. Hp102; H. Miyazono, H. Kikuchi, K. Yoshida, K. Morikawa, K. Tokuyasu, Seikagaku, 61, 1023 (1989)), chondroitinase B (derived from Flavobacterium heparinum; Y. M. Michelacci, C. P. Dietrich, Biochem. Biophys. Res. Commun., 56, 973 (1974), Y. M. Michelacci, C. P. Dietrich, Biochem. J., 151, 121 (1975), K. Maeyama, A. Tawada, A. Ueno, K. Yoshida, Seikagaku, 57, 1189 (1985)), chondroitinase B. C (derived from Flavobacterium sp. Hp102;

H. Miyazono, H. Kikuchi, K. Yoshida, K. Morikawa, K. Tokuyasu, Seikagaku, 61, 1023 (1989)) and the like are known, and any of these chondroitinase may be used.

Also, chondroitinase having the following physical and chemical properties may be used (see, Seikagaku, 67, 737 (1995)):

① Action:

Hydrolyze a N-acetylhexosaminide linkage in glycosaminoglycan. Action on chondroitin sulfate results in the production of saturated chondroitin sulfate oligosaccharides having 12–16 sugars mainly.

② Substrate specificity:

At pH 5, act on chondroitin sulfate, but not on hyaluronic acid, keratan sulfate, heparan sulfate and heparin.

At pH 3.5, act on chondroitin sulfate and hyaluronic acid.

③ Optimum pH for reaction:

Near pH 5 (substrate: chondroitin sulfate derived from shark cartilage (average molecular weight 44000), buffer: 50 mM citric acid-$Na_2HPO_4$ buffer containing 0.15M NaCl, temperature: 37° C.)

④ Isoelectric point:
  Near pH 5
⑤ Molecular weight:
  Approximately 36 kDa, in sodium dodecyl sulfate (SDS)-polyacrylamide gel electrophoresis using a gel wherein polyacrylamide is copolymerized with chondroitin sulfate chains having allyl groups at their ends (zymography; Anal. Biochem. 225, 333–340 (1995))
⑥ Endo-type enzyme
⑦ Derived from human.

This enzyme can be obtained, for example, from the surrounding tissue of human gastric cancer by a conventional extraction or purification method for enzymes. More specifically for the extraction method, extraction by a cell disruption-extraction method such as cutting into small pieces with scissors etc., homogenization, sonication, osmotic shock, freeze-thawing and the like, extraction with surfactants, and combinations thereof can be mentioned. Particularly preferred is a method wherein tissue is cut into small pieces with scissors. Also, more specifically for the purification methods, for example, salting out with ammonium sulfate and sodium sulfate etc., centrifugation, dialysis, ultrafiltration, adsorption chromatography, ion-exchange chromatography, hydrophobic chromatography, reversed phase chromatography, gel filtration, gel permeation chromatography, affinity chromatography, electrophoresis, zymography and the like, and combinations thereof can be mentioned, zymography (Anal. Biochem. 225, 333–340 (1995)) being particularly preferred.

In addition, this enzyme can be purified by chromatography with a carrier having heparin as a ligand, since it can be adsorbed to Heparin-Sepharose (Pharmacia).

Furthermore, chondroitinase having the above physical and chemical properties can be also obtained by cloning a gene of this enzyme according to known per se methods, and transfecting it into an appropriate host, followed by the expression. For example, this enzyme may be obtained by the isolation of DNA which codes for this enzyme from human DNA library using a specific chondroitin sulfate degradation activity of said enzyme as an indicator, the insertion into a vector by means of recombinant DNA techniques, the transfection into host cells, and the expression. Alternatively, cloning may be carried out by generating a specific antibody to this enzyme and using said antibody. In addition, cloning may be carried out by the determination of the N-terminal amino acid sequence of this enzyme and the use of DNA or oligonucleotide having a nucleotide sequence deduced from this sequence as a probe. The expressed enzyme can be recovered by means of the extraction and purification methods as described above.

Moreover, chondroitinase having the following physical and chemical properties can be also used (see, J. Biol. Chem., 272, 9123–9130 (1997)).
① Action:
  (1) Hydrolyze a N-acetylhexosaminide linkage in glycosaminoglycan, and upon complete degradation, only unsaturated glycosaminoglycan disaccharide is substantially produced.
  (2) Exo-type enzyme
② Substrate specificity:
  Act on any of chondroitin, chondroitin 4-sulfate, chondroitin 6-sulfate, chondroitin sulfate D, chondroitin sulfate E, dermatan sulfate, chondroitin 6-sulfate hexasaccharide, chondroitin 6-sulfate tetrasaccharide, and chondroitin sulfate chain moiety in chondroitin sulfate proteoglycan.
  Not act on keratan sulfate, heparin and heparan sulfate.
③ Molecular weight:
  Approximately 105 kDa, in SDS-polyacrylamide gel electrophoresis under reducing conditions.
④ Amino acid composition:
  Cystine is detected, by the amino acid analysis of acid hydrolysate from this chondroitinase. This shows that this chondroitinase contains a cysteine residue and/or a cystine residue.
⑤ N-terminal amino acid:
  The N-terminal amino acid is leucine.
⑥ Isoelectric point:
  Approximately pH 8.45 (Isoelectric focusing)
⑦ Optimum temperature:
  Near 40° C. (substrate: chondroitin 6-sulfate, buffer: Tris-HCl buffer, pH: 8.0)
⑧ Optimum pH for reaction:
  Near pH 8 (substrate: chondroitin 6-sulfate, buffer: Tris-HCl buffer, temperature: 37° C.)

This enzyme is known as chondroitin sulfate ABC exolyase or exochondroitinase ABC, and a process for its preparation and the like are also known (A. Hamai, N. Hashimoto, H. Mochizuki, F. Kato, Y. Makiguchi, K. Horie and S. Suzuki, J. Biol. Chem., 272, 9123–9130 (1997)).

These various types of chondroitinase are mentioned only as an example, and the present invention is not deemed to be limited to such chondroitinase. Chondroitinase used in the invention may be one chondroitinase or a combination of more than one chondroitinase, both of which are incorporated into the term "chondroitinase" herein.

In the present invention, chondroitinase ABC is preferably used in some cases. Among chondroitinase ABC, chondroitinase ABC derived from *Proteus vulgaris* is particularly preferred for use.

Preferably, chondroitinase is purified to the extent that it can be used as a pharmaceutical product, and does not substantially contain pharmaceutically unacceptable substance. That is, preferably, chondroitinase is purified chondroitinase having enzyme specific activity of 300 U/mg protein or more. More preferably, chondroitinase is purified chondroitinase having enzyme specific activity of 300 U/mg protein or more, not containing endotoxin substantially, and having a nucleic acid content and a protease content both of which are below the detection limit. Purified chondroitinase ABC having these properties is particularly preferable. Herein, one unit (U) of chondroitinase is the amount of the enzyme required to liberate 1 micromole of a reaction product from chondroitin sulfate in one minute under the conditions of near optimum pH and optimum temperature. For example, for chondroitinase ABC, one unit is the amount of the enzyme needed to liberate 1 micromole of unsaturated disaccharide from chondroitin sulfate in one minute at pH 8.0 and 37° C. By using chondroitinase with enzyme specific activity of 300 U/mg protein or more, when administered in vivo as a pharmaceutical product for injection, it can adequately degrade proteoglycan at the target site (e.g. intervertebral disc of mammals, preferably humans, with herniation) without affecting the surrounding tissue, thus being able to afford a pharmaceutical product with high safety and high efficiency.

Most preferable chondroitinase used in pharmaceutical compositions of the invention is purified chondroitinase ABC having the following properties.
(i) The molecular weight is approximately 100,000 dalton in the measurements by SDS-polyacrylamide gel electrophoresis (SDS-PAGE) (under both reducing and non-reducing conditions) and by gel filtration.
(ii) The isoelectric point is about pH 8.2 and about pH 8.5.

(iii) The optimum pH is 8.0-8.2 (substrate: chondroitin sulfate C, buffer: Tris-HCl buffer), and the optimum temperature is 37° C.
(iv) The activity is inhibited by $Zn^{2+}$, $Ni^{2+}$, $Fe^{3+}$ and $Cu^{2+}$.
(v) The N-terminal amino acid is alanine, and the C-terminal amino acid is proline.
(vi) A single band appears in SDS-PAGE, and a single peak is also obtained in high performance liquid chromatography (gel filtration and cation-exchange).
(vii) No endotoxin is contained substantially, and a nucleic acid content and a protease content are below the detection limit.
(viii) Can be crystalized.
(ix) The specific activity is 300 U/mg or more.

Such chondroitinase ABC may be obtained, for example, according to the methods described in U.S. Pat. No. 5,496,718 and EP-A-576,294.

Pharmaceutical carrier:

As pharmaceutical carriers in pharmaceutical compositions of the invention, used are those wherein an amount of reducing impurities per 1 g of said pharmaceutical carrier is 0.4 mL or less, preferably 0.36 mL or less, as a titer by a titration method with 0.01 N ammonium ceric nitrate. In addition, those wherein a peroxide content is 20 ppm or less, particularly 18.5 ppm or less are more preferred. Furthermore, pharmaceutical carriers used in pharmaceutical compositions of the invention are preferably those which are treated with activated carbon.

Herein, the term "a titration method with 0.01 N ammonium ceric nitrate" refers to a method wherein 2 g of a pharmaceutical carrier is dissolved in 25 mL of warm water, 25 mL of dilute sulfuric acid and 0.1 mL of ferroin (tris(1, 10-phenanthroline) iron (II) complex: $[Fe(C_{12}H_8N_2)_3]^{2+}$) are added, and the mixture is titrated with 0.01 N ammonium ceric nitrate until the color is changed to greenish-blue from red and held for 30 seconds. By measuring the volume of 0.01 N ammonium ceric nitrate used for the titration, and then by converting it to a titer per 1 g of a pharmaceutical carrier, an amount of reducing impurities can be obtained.

As examples of pharmaceutical carriers, additives, which are generally used for pharmaceutical products, such as conventional diluents, binders, lubricants, coloring agents, disintegrating agents, buffer agents, isotonizing agents, preservants, anesthetics and the like are given.

Preferably, pharmaceutical carriers used in pharmaceutical compositions of the invention are purified to the extent that they can be used as a pharmaceutical product, and do not substantially contain pharmaceutically unacceptable substance. More specifically for such pharmaceutical carriers, for example, dextran, sucrose, lactose, maltose, xylose, trehalose, mannitol, xylitol, sorbitol, inositol, serum albumin, gelatin, creatinine, polyethylene glycol, non-ionic surfactants (e.g. polyoxyethylene sorbitan fatty acid esters, polyoxyethylene hardened castor oil, sucrose fatty acid esters, polyoxyethylene polyoxypropylene glycol) and the like can be mentioned. As examples of the above polyoxyethylene sorbitan fatty acid esters (polysorbates), polyoxyethylene sorbitan (the polymerization degree of ethylene oxide: about 20) monolaurate, monopalmitate, monooleate, monostearate, trioleate and the like can be given. As commercial products, Polysorbate 80 (polyoxyethylene sorbitan monooleate (20 E. O.)), Polysorbate 60 (polyoxyethylene sorbitan monostearate (20 E. O.)), Polysorbate 40 (polyoxyethylene sorbitan monopalmitate (20 E. O.)), Polysorbate 20 (polyoxyethylene sorbitan monolaurate (20 E. O.)), Polysorbate 21, 81, 65, 85 and the like can be named (Here, 20 E. O. means that the polymerization degree of ethylene oxide in polyoxyethylene moiety is about 20). As examples of polyoxyethylene hardened caster oil, commercially available HCO-10$^R$, HCO-50$^R$, HCO-60$^R$ (Nikko Chemicals Co., Ltd.) and the like can be given. As sucrose fatty acid esters, commercially available DK ester F-160$^R$ (Dai-ichi Kogyo Seiyaku Co., Ltd.), Ryoto sugar ester$^R$ (Mitsubishi Kagaku Foods) and the like can be mentioned. As polyoxyethylene polyoxypropylene glycol (poloxamer), commercially available Pluronic F-68 (Asahi Denka Kogyo K.K.) and the like can be given.

Buffer agents can be any of those which are physiologically acceptable, and are not particularly limited. For example, buffer agents containing one or more of hydrochloric acid, sodium hydroxide, sodium carbonate, sodium hydrogencarbonate, phosphoric acid, potassium dihydrogenphosphate, dipotassium hydrogen-phosphate, sodium dihydrogenphosphate, disodium hydrogen-phosphate, aminoacetic acid, sodium benzoate, citric acid, sodium citrate, acetic acid, sodium acetate, tartaric acid, sodium tartrate, lactic acid, sodium lactate, ethanolamine, arginine, ethylenediamine and the like can be mentioned.

In pharmaceutical compositions of the invention, these pharmaceutical carriers may be used suitably in combination. Among those, polyethylene glycol and/or sucrose, or polyoxyethylene sorbitan fatty acid esters, particularly polyoxyethylene sorbitan monooleate (20 E. O.), is preferred.

Among these, polyethylene glycol is particularly suitable when pharmaceutical compositions of the invention are provided in the form of freeze-dried preparations, since it is effective in preventing a decrease in enzyme activity of chondroitinase after freeze-drying, in keeping a water content low in freeze-dried preparations, in giving a clear solution without particulate matter upon reconstituting freeze-dried preparations, in producing good appearance of cake after freeze-drying, and in yielding a relatively little decrease in enzyme activity of chondroitinase during long-term storage of freeze-dried preparations.

Also, a mixture of polyethylene glycol and sucrose is particularly preferable when pharmaceutical compositions of the invention are provided in the form of freeze-dried preparations, since it is effective in preventing a decrease in enzyme activity of chondroitinase after freeze-drying, in keeping a water content low in freeze-dried preparations, in giving a clear solution without particulate matter upon reconstituting freeze-dried preparations, in producing good appearance of cake after freeze-drying, and in yielding a very little decrease in enzyme activity of chondroitinase during long-term storage of freeze-dried preparations.

As polyethylene glycol that can be used in the above cases, it is not particularly limited as far as an amount of reducing impurities per 1 g of said polyethylene glycol is 0.4 mL or less, preferably 0.36 mL or less, as a titer by a titration method with 0.01 N ammonium ceric nitrate, but in addition, it is more preferable to use those polyethylene glycol wherein a peroxide content is 20 ppm or less, and particularly 18.5 ppm or less.

Furthermore, preferred polyethylene glycol is those having an average molecular weight of 200–25000, more preferred is those which are solid at ordinary room temperature, for example, having an average molecular weight of 2000–9000, particularly preferably of 2000–4000, and especially preferably of 3000–4000. As polyethylene glycol having an average molecular weight of 3000–4000, for example, those having an average molecular weight of 3250, 3350 and 4000 can be mentioned.

Sucrose used is also those wherein an amount of reducing impurities per 1 g of said sucrose is 0.4 mL or less, preferably 0.36 mL or less, as a titer by a titration method with 0.01 N ammonium ceric nitrate. Furthermore, it is preferred to use those wherein a peroxide content is 20 ppm or less, and particularly 18.5 ppm or less.

Since the inventors have proved that a endotoxin content in commercially available sucrose is generally high, it is preferred to treat it with activated carbon and the like, so that the concentration of endotoxin in a 10% (w/w) sucrose solution becomes 0.03 EU/mL or less, desirably 0.01 EU/mL or less, and more desirably 0.006 EU/mL or less.

The concentration of endotoxin in sucrose can be determined using known per se test methods for endotoxin, but the Limulus test with horseshoe crab amebocyte lysate component is preferred. As Limulus reagents used in the Limulus test, those specific to endotoxin are preferable. As Limulus reagents, for example, the following commercially available Limulus reagents may be used; Toxicolor System LS-6$^R$, LS-20$^R$, LS-200$^R$, Endospecy ES-6$^R$, Endospecy ES-200$^R$ (all from Seikagaku Corporation), Limulus ES-II Test Wako$^R$, Limulus ES-II Single Test Wako$^R$, Limulus ES-III Test Wako$^R$, Limulus ES-J Test Wako$^r$ (all from Wako Pure Chemical Industries, Ltd.).

In case polyethylene glycol and/or sucrose are/is used as a pharmaceutical carrier, generally, they are mixed such that the weight ratio of polyethylene glycol/sucrose is preferably about 0/1–10/1, and in case a mixture of polyethylene glycol and sucrose is used as a pharmaceutical carrier, they are mixed such that the weight ratio of polyethylene glycol/sucrose is preferably about 1/10–10/1, more preferably about 1.5/1–3/1, and particularly preferably about 2/1.

In this case, it is also important to make an amount of reducing impurities in a mixture of polyethylene glycol and sucrose 0.4 mL or less, preferably 0.36 mL or less, per 1 g of said mixture as a titer by a titration method with 0.01 N of ammonium ceric nitrate. Furthermore, it is more preferable to make a peroxide content in a mixture of polyethylene glycol and sucrose 20 ppm or less, and particularly 18.5 ppm or less.

In case polyoxyethylene sorbitan fatty acid ester is used as a pharmaceutical carrier, polyoxyethylene sorbitan fatty acid ester wherein an amount of reducing impurities per 1 g of said ester is 0.4 mL or less, preferably 0.36 mL or less, as a titer by a titration method with 0.01 N of ammonium ceric nitrate is employed. Furthermore, it is more preferable to use those wherein a peroxide content in said ester is 20 ppm or less, and particularly 18.5 ppm or less.

The amount of peroxide contained in a pharmaceutical carrier can be determined by a method wherein 1 g of a pharmaceutical carrier is accurately weighed, distilled water added to a volume of 10 mL, that is, giving an aqueous 10% (w/v) solution, 0.25 mL of 20% (v/v) sulfuric acid and 0.15 mL of 1 M TiSO$_4$ (BDH) are added to 0.8 mL of this aqueous solution, and the absorption in the ultraviolet region at 408 nm is measured, followed by calculating the concentration of H$_2$O$_2$ on the basis of a calibration curve which has been generated using known concentrations of H$_2$O$_2$.

The amount of reducing impurities and/or the amount of peroxide contained in a pharmaceutical carrier which is desirably used in pharmaceutical compositions of the invention can be lowered, for example, by treating a pharmaceutical carrier with activated carbon in accordance with conventional methods. The amount of peroxide can be also lowered by heat-treatment of a pharmaceutical carrier.

The mixing ratio of chondroitinase and a pharmaceutical carrier in pharmaceutical compositions of the invention is not particularly limited, and can be suitably determined by those skilled in the art depending on the amount for administration, the form of pharmaceutical compositions of the invention and the like. For example, when pharmaceutical compositions of the invention is provided (stored) in the form of freeze-dried preparations, a preferred content of chondroitinase in pharmaceutical compositions of the invention is such that the shape of freeze-dried cake can be kept.

Pharmaceutical compositions of the invention can be prepared by known per se methods using chondroitinase and a pharmaceutical carrier as described above. Pharmaceutical compositions of the invention may be also in either solution, frozen, or dried form.

Pharmaceutical compositions of the invention, when provided in solution form, can be prepared, for example, by making a pH-adjusted buffer solution, and adding the above-mentioned chondroitinase and a pharmaceutical carrier to give a solution containing 5 U/mL or more, more preferably 10–400 U/mL chondroitinase, and if necessary, followed by sterilization by filtration.

Pharmaceutical compositions of the invention, when provided in frozen form, can be prepared, for example, by freezing pharmaceutical compositions of the invention in solution form as described above, for example, at −80–18° C.

Pharmaceutical compositions of the invention, when provided in dried form, can be prepared, for example, by drying pharmaceutical compositions of the invention in solution form as described above under non-heating conditions such as freeze-drying and the like.

Among these, preferred form of pharmaceutical compositions of the invention is dried from, and more preferred is freeze-dried form, that is, freeze-dried preparations.

It is desirable to adjust the pH of pharmaceutical compositions of the invention usually to pH 5–9, and preferably to pH 6–8, in solution form (in case pharmaceutical compositions of the invention are in frozen form, solution form before freezing and after thawing, and in case pharmaceutical compositions of the invention are freeze-dried compositions, solution form before freeze-drying and after reconstituted by the addition of a solvent). For this purpose, a buffer agent which is capable of stabilizing the pH in said pH region is usually mixed into pharmaceutical compositions of the invention. As said buffer agents, any physiologically acceptable buffer agents may be used, without particular limitation, and for example, hydrochloric acid, sodium hydroxide, sodium carbonate, sodium hydro-gencarbonate, phosphoric acid, potassium dihydrogenphosphate, dipotassium hydrogenphosphate, sodium dihydrogenphosphate, disodium hydrogenphosphate, aminoacetic acid, sodium benzoate, citric acid, sodium citrate, acetic acid, sodium acetate, tartaric acid, sodium tartarate, lactic acid, sodium lactate, ethanolamine, arginine, ethylenediamine, or mixtures thereof can be mentioned. Phosphate buffer solution (agent) is particularly preferred. By means of these buffer agents, the pH of pharmaceutical compositions of the invention can be adjusted to and stabilized at the pH range of pH 5–9, and preferably pH 6–8, in solution form. When the pH is lower than 5 or higher than 9, chondroitinase may be inactivated, or insoluble matter may be produced in solution form. The concentration of a buffer agent in pharmaceutical compositions of the invention may be made to 1 mM or more, and preferably 10-50 mM. Pharmaceutical compositions of the invention may include, in addition to a buffer agent, components required for isotonization (salts such as sodium chloride, etc., sugars, and the like), preservants, anesthetics and the like.

The pharmaceutical compositions of the invention may be used as final dosage form to be administered as a pharmaceutical product as such, or as a material for final dosage form of other pharmaceutical products, for example, solution preparations, freeze-dried preparations and the like.

The pharmaceutical compositions of the invention are mainly used as injection preparations containing chondroitinase as the active ingredient. When pharmaceutical compositions of the invention are provided as injection preparations in solution form, the pharmaceutical compositions of the invention in solution form, prepared by the abovementioned method, may be filled and sealed in appropriate containers such as ampules, vials, syringes for injection and the like, distributed as such or stored, and served as injection preparations for administration.

When pharmaceutical compositions of the invention are provided as injection preparations in frozen form, the pharmaceutical compositions of the invention in frozen form, prepared by the abovementioned method, may be filled and sealed in appropriate containers such as ampules, vials, syringes for injection and the like, distributed as such or stored, and melted before administration to serve as injection preparations.

Preferably, the distribution and storage are carried out at the temperature of −80° C. to −25° C.

When pharmaceutical compositions of the invention are provided as injection preparations in dried form, the pharmaceutical compositions of the invention in dried form, prepared by the abovementioned method, may be filled and sealed in appropriate containers such as ampules, vials, syringes for injection and the like, distributed as such or stored, reconstituted with water for injection, physiological saline, aqueous glucose solution or aqueous sorbitol solution, and the like before administration to serve as injection preparations. The pharmaceutical compositions of the invention in dried form may be provided together with a solvent for reconstitution.

Among the abovementioned injection preparations, dried form is preferable, and freeze-dried form is more preferable. That is, particularly preferred pharmaceutical compositions of the invention are in the form of freeze-dried compositions for injection.

When pharmaceutical compositions of the invention is filled or sealed in appropriate containers such as ampules, vials, syringes for injection and the like, it is preferable to fill or seal inert gas such as nitrogen gas, inert gas and the like together to prevent chemical reactions, especially oxidation, of pharmaceutical compositions of the invention.

The material of containers such as ampules, vials, syringes for injection and the like, wherein pharmaceutical compositions of the invention can be filled or sealed, is not particularly limited as far as it does not affect the pharmaceutical compositions of the invention and is pharmaceutically acceptable, but glass is preferable.

The pharmaceutical compositions of the invention, which is provided as freeze-dried compositions for injection, have a special feature that a decrease in enzymatic activity of chondroitinase is very little between before and after freeze-drying. More specifically, after freeze-drying, pharmaceutical compositions of the invention can retain 90% or more of enzyme activity of chondroitinase before freeze-drying. The enzyme activity of chondroitinase can be determined, for example, by a method wherein chondroitinase is allowed to act at 37° C. using chondroitin sulfate as a substrate, and produced unsaturated disaccharides having significant absorption in the ultraviolet region is measured by absorption spectrophotometry (e.g. the absorbance at 232 nm).

It is generally anticipated that the stability of freeze-dried preparations is improved as a water content is lowered, and pharmaceutically a water content in freeze-dried preparations is usually set to 3% (w/w) or less as a goal. Therefore, in case pharmaceutical compositions of the invention are provided in the form of freeze-dried compositions for injection, a water content in freeze-dried compositions for injection of the invention is also preferably set to 3% (w/w) or less. The content of water can be measured, for example, by the Loss on Drying Test (TG method) wherein samples are heated under the following condition, the weight before and after heating is weighed by a micro-balance, and the decreased weight considered as the amount of water (heating condition: samples are heated from 25° C. to 105° C. at 2.5° C./minute, and held at 105° C. for 20 minutes after reaching to 105° C.), or the Karl Fischer Method wherein samples are stirred in methanol for 3 minutes, water is extracted, coulometric titration performed on the extracted water, and the required electrical quantity (coulomb) converted to the amount of water.

Preferably, pharmaceutical compositions of the invention, provided in the form of freeze-dried compositions for injection, are clear and do not contain particulate matter, when said freeze-dried compositions are reconstituted with physiological saline. The clearness and the absence of particulate matter can be easily found by visual observation.

The pharmaceutical compositions of the invention, provided in the form of freeze-dried compositions for injection, have an advantage that a decrease in enzyme activity of chondroitinase is very little even after long-term storage at ordinary room temperature. For example, the pharmaceutical compositions of the invention can retain 90% or more of the enzyme activity of chondroitinase at the beginning of storage, when stored in a glass container filled with nitrogen for 30 days at 40° C.

The pharmaceutical compositions of the invention can be employed, for example, in the treatment of disc herniation, thereby agents of the invention being provided. The agents of the invention can be used in the intervertebral disc dissolution method wherein nucleus pulposus is dissolved by injecting an agent into the intervertebral disc of mammals, preferably humans, with herniation. Although a dose should be determined individually depending on the symptom, age and the like, and not generically specified, normally, an amount of about 0.1–100 U per dose can be injected, in case chondroitinase ABC is used as chondroitinase.

EXAMPLES

Hereinbelow, the present invention is described further specifically by the examples on pharmaceutical compositions of the invention containing chondroitinase ABC, but said examples are presented only to illustrate the invention, and are not intended to limit the scope of the invention.

Chondroitinase ABC used in the examples was prepared according to the methods described in U.S. Pat. No. 5,496, 718 and EP-A-576,294.

This chondroitinase ABC gave a single band in sodium dodecyl sulfate-polyacrylamide gel electrophoresis (SDS-PAGE), and also showed a single peak in high performance liquid chromatography (gel filtration and cation exchange). These results confirmed that this chondroitinase ABC was completely purified.

The content of endotoxin per 100 U of this chondroitinase ABC measured with Toxicolor System (Seikagaku Corporation) was 3.4 pg (0.00986 EU: EU means the unit of endotoxin, and 1 pg=0.0029 EU), thus very little, and substantially no endotoxin was contained.

The amount of nucleic acid (DNA) in this chondroitinase ABC was examined using the Threshold method (DNA analyzer: Threshold (Molecular Device)), but no DNA was detected.

The amount of protease in this chondroitinase ABC was examined using FITC (fluorescein isothiocyanate)-casein as a substrate, but no protease was detected.

The enzymatic activity of chondroitinase ABC was determined by the following method.

Using 1.2 mg of chondroitin sulfate C as a substrate, to a 50 mM Tris-HCl buffer solution (pH 8) containing 50 mM sodium acetate, and 10 µg of casein, an enzyme sample (chondroitinase ABC) was added, the reaction carried out at 37° C. for 10 minutes, then terminated by the addition of 0.05 M hydrochloric acid with pH 1.8, and the absorbance in the ultraviolet region (at 232 nm) was measured. On the other hand, as a control, a heat-denatured enzyme sample was held in a substrate solution having the abovementioned composition, similar procedures performed, and the absorbance at 232 nm was measured. The amount of unsaturated disaccharide produced by the action of chondroitinase ABC was calculated from an increase in the absorbance compared to control. One unit (U) of an enzyme was defined as an amount of the enzyme required to catalyze a reaction wherein 1 micromole of unsaturated disaccharide is released for 1 minute under the abovementioned reaction condition, considering the millimolar absorption coefficient of 2-acetamido-2-deoxy-3-0-($\beta$-D-gluco-4-enepyranosyluronic acid)-6-0-sulfo-D-galactose as 5.5.

As a result, this chondroitinase ABC was verified to have specific activity of 300 U/mg protein or more.

Example 1

Preparation of pharmaceutical compositions of the invention consisting of chondroitinase ABC and Polysorbate 80

Polysorbate 80 was obtained from several manufactures, and an amount of reducing impurities and a concentration of peroxide in 1 g of Polysorbate 80 were determined in accordance with the abovementioned methods.

Then, sodium chloride (0.75%), the above highly purified chondroitinase ABC (specific activity 350 U/mg; final concentration 25 U/mL) and Polysorbate 80 (0.15% (w/w)) were dissolved in a 20 mM phosphate buffer solution (pH 7) to prepare a composition (solution). The solution was sterilized by filtration using a membrane filter (pore size 0.22 µm; Millex GV, MILLIPORE), and every 2 mL was filled into sterilized glass ampules, which were subsequently sealed.

The sealed glass ampules were stored for one month at 25° C., and then evaluation was carried out by the following methods.

Evaluation methods:
(1) Appearance: Visual observation was made at a position of luminous intensity of about 1000 luxes, right under an incandescent electric bulb with a white paper and a black paper on the background,
(2) Measurement of enzyme activity of chondroitinase ABC: Using a solution before storage or a solution after storage as an enzyme sample in the above-mentioned method for the measurement of enzyme activity, the measurement was carried out.

The percentage of enzyme activity of a solution after storage (Post solution) to that of a solution before storage (Pre solution) was calculated with the following equation, and variations in enzyme activity by one month storage at 25° C. were compared.

[Enzyme activity of Post solution/Enzyme activity of Pre solution]×100 (%)

Results are shown in Table 1 as "stability", along with the results from the measurements of an amount of reducing impurities and a concentration of peroxide in 1 g of a pharmaceutical carrier (Polysorbate 80). Here, "N/T" in Table 1 means not being tested.

TABLE 1

| Pharmaceutical carrier (Polysorbate 80) | Amount of reducing impurities (mL) (titer per 1 g) | Concentration of peroxide (ppm) | Stability (%) |
| --- | --- | --- | --- |
| A | 0.27 | N/T | 87 |
| B | 0.36 | 16.0 | 85 |
| C | 0.33 | N/T | 84 |
| D | 0.28 | N/T | 83 |
| E | 0.08 | N/T | 78 |
| F | 0.29 | N/T | 75 |
| G | 0.24 | 18.5 | 63 |
| H | 0.51 | N/T | 36 |
| I | 0.43 | 29.5 | 32 |
| J | 0.45 | 24.5 | 24 |
| K | 2.21 | N/T | 5.3 |
| L | 2.55 | 115.5 | 5.1 |

As a result, pharmaceutical compositions wherein an amount of reducing impurities in 1 g of a pharmaceutical carrier (Polysorbate 80) was 0.4 mL or less as a titer by a titration method with 0.01 N ammonium ceric nitrate (A-G in Table 1) retained 60% or more of the activity after one month storage at 25° C. in solution form.

In contrast, for pharmaceutical compositions wherein an amount of reducing impurities in 1 g of a pharmaceutical carrier (Polysorbate 80) was 0.4 mL or more as a titer by a titration method with 0.01 N ammonium ceric nitrate (H-L in Table 1), the activity after one month storage at 25° C. in solution form was 40% or less.

All samples were colorless and clear, and no production of insoluble particulate matter was observed after one month storage at 25° C.

Example 2

Decreasing effects of the treatment with activated carbon on an amount of reducing impurities and a concentration of peroxide Effects of the treatment of Polysorbate 80 with activated carbon were examined using Polysorbate 80 of product B and Polysorbate 80 of product L in the above Table 1.

After 10 g of each Polysorbate 80 of product B and product L was dissolved in water to a volume of 100 mL, to each solution added 10 g of activated carbon that had been heat-treated for 5 hours at 250° C. The mixture was then stirred for 30 minutes under room temperature, and the activated carbon was filtered off, giving activated carbon treated Polysorbate 80.

For Polysorbate 80 thus obtained, a content of reducing impurities and a content of peroxide (both of which were measured by similar methods as described above) were determined before and after the treatment with activated carbon. Then, compositions were prepared with formulation described in Example 1, and the stability of chondroitinase ABC was tested after one month storage at 25° C. Results are shown in Table 2.

TABLE 2

| | Pharmaceutical carrier (Polysorbate 80) | Amount of reducing impurities (mL) (Titer per 1 g) | Concentration of peroxide (ppm) | Stability (%) |
|---|---|---|---|---|
| B | Before activated carbon treatment | 0.36 | 16.0 | 82 |
| | After activated carbon treatment | 0.09 | 15.0 | 91 |
| L | Before activated carbon treatment | 2.55 | 115.5 | 7.2 |
| | After activated carbon treatment | 0.4 | 90 | 87 |

These results show that an amount of reducing impurities and a content of peroxide decreased by the treatment with activated carbon. In particular, a decrease in an amount of reducing impurities by the treatment was remarkable.

It was also shown that chondroitinase ABC activity was retained stably in the pharmaceutical compositions which were prepared using Polysorbate 80 with activated carbon treatment, compared to the pharmaceutical compositions which were prepared using Polysorbate 80 without the treatment.

Example 3

Preparation of pharmaceutical compositions of the invention (freeze-dried preparations) consisting of chondroitinase ABC and poly-ethylene glycol (1) Polyethylene glycol used in this example Polyethylene glycol 4000 (PEG 4000, average molecular weight 2600–3800; Wako Pure Chemical Industries, Ltd., first grade, Lot. No. CAE 0369) was dissolved in endotoxin-free distilled water (water for injection), this aqueous solution treated with activated carbon, and an amount of reducing impurities and a content of peroxide were measured according to the abovementioned methods. As a result, the amount of reducing impurities in a 4% (w/v) polyethylene glycol solution was 0 mL as a titer, and the content of peroxide in a 6.66% (w/v) polyethylene glycol solution was below the detection limit (below 0.0017% (w/v).

(2) Test method (Stability test)

Chondroitinase ABC (final concentration 40 U/mL) and polyethylene glycol 4000 (final concentration 1% (w/w)) were dissolved in a 10 mM phosphate buffer solution (pH 7), and every 0.5 mL was filled into vials (giving 20 U/vial as chondroitinase ABC), which were subsequently freeze-dried. Freeze-drying is performed as follows: cool-freezing from room temperature to −45° C., primary drying for 12 hours under reduced pressure (60 mTorr), heat-up to 25° C. (12 hours), and secondary drying for 10 hours at 25° C. After the drying, pressure was restored with nitrogen gas, and vials were capped.

Then, the percentage of "the enzyme activity of a reconstituted solution of a freeze-dried composition after stored for 30 days under 40° C." to "the enzyme activity of a solution before freeze-drying" was obtained in accordance with the following procedure. Enzyme activity of chondroitinase after freeze-drying (hereinbelow, "enzyme activity of chondroitinase" may be simply called as "enzyme activity"), appearance of cake, re-solubility and a water content were evaluated.

Enzyme activity was determined using a solution before freeze-drying or a reconstituted solution with physiological saline after freeze-drying as an enzyme sample, in accordance with the abovementioned method for the measurement of enzyme activity.

The percentage of the enzyme activity of a reconstituted solution after freeze-drying (Post-FD solution) to the enzyme activity of a solution before freeze-drying (Pre-FD solution) was calculated with the following equation, and the variations in enzyme activity at the time of freeze-drying and those during subsequent storage were compared.

[Enzyme activity of Post-FD/Enzyme activity of Pre-FD]×100 %

Appearance of cake was visually observed. When the appearance of dried cake after freeze-drying was in good tablet form, it was identified as "good", and when the appearance of dried cake after freeze-drying was not in good tablet form, it was identified as "poor".

Re-solubility was determined after freeze-drying by observing the solubility when reconstituted with 2 mL of physiological saline and the appearance of the solution after reconstituted. More specifically, reconstitution was first confirmed within one minute after the addition of physiological saline. When insoluble particulate matter was found in the dissolved solution by visual observation, the result was identified as "+", and when the solution was clear and no particulate matter was observed, the result was identified as "−". The content of water was measured according to the abovementioned TG Method.

(3) Results

The results of stability test with freeze-dried preparations consisting of a combination of chondroitinase ABC and polyethylene glycol 4000 showed that in freeze-dried preparations consisting of a combination of chondroitinase ABC and polyethylene glycol 4000, the enzyme activity decreased little even after storage for 30 days under 40° C. (the percentage of enzyme activity of Post-FD to that of Pre-FD is 76.1 %) and was retained very stably.

Also, a water content in the freeze-dried preparations was as low as 3% (w/w) or less, appearance of cake was "good", and re-solubility was "−".

Example 4

Preparation of pharmaceutical compositions of the invention (freeze-dried preparations) consisting of chondroitinase ABC, polyethylene glycol and sucrose (1) Polyethylene glycol used in this example Polyethylene glycol 4000 with activated carbon treatment was used in the same way as in example 3.

(2) Sucrose used in this example

Sucrose (refined white sugar: Dai-Nippon Meiji Sugar Co., Ltd., Lot. No. 910403) was dissolved in endotoxin-free distilled water (water for injection) so as to be 10% (w/w). The concentration of endotoxin in said aqueous solution was measured with Toxicolor System (Seikagaku Corporation), resulting in 6.66 EU/mL (2296.49 pg/mL). The aqueous solution was treated with activated carbon, and the concentration of endotoxin was again measured similarly. The result was 0.001 EU/mL (0.43 pg/mL). Also, a content of peroxide and an amount of reducing impurities in this activated carbon treated sucrose were measured according to the abovementioned procedures. As a result, the amount of reducing impurities in a 4% (w/v) sucrose solution was 0 mL as a titer and no peroxide was detected in a 6.66% (w/v) sucrose solution.

(3) Test method (3-1) Preliminary test

As a preliminary test, samples that contain only pharmaceutical carriers without the addition of chondroitinase ABC were first prepared, and evaluated for appearance of the freeze-dried preparations. More specifically, as a pharmaceutical carrier sucrose and polyethylene glycol 4000 were mixed at the ratios shown in Table 3, and dissolved in a 10 mM phosphate buffer solution (pH 7). Appearance of cake after freeze-drying was evaluated using freeze-dried preparations as a sample.

TABLE 3

| Sucrose/Polyethylene glycol |
|---|
| 1/1 |
| 1/2 |
| 5/1 |
| 5/2 |
| 10/1 |
| 10/2 |

Freeze-drying was carried out as follows: cool-freezing from room temperature to −45° C., primary drying for 12 hours under reduced pressure (60 mTorr), heat-up to 25° C. (12 hours), and secondary drying for 10 hours at 25° C. After the drying, pressure was restored with nitrogen gas, and vials were capped.

As a result, a composition wherein the mixed ratio of sucrose and polyethylene glycol was ½ did not cause melt back, collapse and shrink.

(3-2) Main test (Stability test)

Chondroitinase ABC (final concentration 20 U/mL), sucrose (final concentration 1% (w/w)) and polyethylene glycol 4000 (final concentration 2% (w/w)) were dissolved in a 10 mM phosphate buffer solution (pH 7), every 0.5 mL was filled into vials (giving 10 U/vial as chondroitinase ABC), which were subsequently freeze-dried. Freeze-drying was performed as follows: cool-freezing from room temperature to −45° C., primary drying for 12 hours under reduced pressure (60 mTorr), heat-up to 25° C. (12 hours), and secondary drying for 10 hours at 25° C. After freeze-drying, pressure was restored with nitrogen gas, and vials were capped.

After this, the test was performed in the same way as "stability test" described in example 3.

(4) Results

The results of stability test (storage at 40° C., for 30 days) with freeze-dried preparations consisting of a combination of chondroitinase ABC, sucrose and polyethylene glycol 4000 showed that in freeze-dried preparations consisting of a combination of chondroitinase ABC, sucrose and polyethylene glycol 4000, the enzyme activity decreased little even after storage for 30 days at 40° C. (the percentage of enzyme activity in Post-FD to that in Pre-FD was 90.9%) and was retained very stably.

Also, a water content in the freeze-dried preparations was as low as 1.5% (w/w) or less, appearance of cake was "good", and re-solubility was "−".

As mentioned above, pharmaceutical compositions of the invention consist of chondroitinase, preferably chondroitinase with high specific activity and high purity, and a pharmaceutical carrier wherein an amount of reducing impurities is 0.4 mL or less per 1 g as a titer by a titration method with 0.01 N ammonium ceric nitrate and desirably a concentration of peroxide is 20 ppm or less.

By selecting such constitution for compositions, the present invention can provide pharmaceutical compositions wherein a decrease in enzyme activity of chondroitinase is very little after long-term storage. Furthermore, by using pharmaceutical compositions of the invention, the invention can provide pharmaceutical products, particularly agents for the treatment of disc herniation, which are safe, effective, easy to handle and can be stored for long time.

We claim:

1. A pharmaceutical composition which comprises chondroitinase and a pharmaceutical carrier, wherein the pharmaceutical carrier, before combining with the chondroitinase, is treated with activated carbon, whereby, the amount of reducing impurities contained in 1 g of said pharmaceutical carrier is 0.4 mL or less as a titer by a titration method with 0.01 N ammonium ceric nitrate.

2. The pharmaceutical composition according to claim 1, wherein the peroxide content in the pharmaceutical carrier is 20 ppm or less.

3. The pharmaceutical composition according to claim 1, wherein the amount of reducing impurities contained in 1 g of the pharmaceutical carrier is 0.36 mL or less as a titer by a titration method with 0.01 N ammonium ceric nitrate.

4. The pharmaceutical composition according to claim 1, wherein the pharmaceutical carrier comprises sucrose.

5. The pharmaceutical composition according to claim 1, wherein the pharmaceutical carrier comprises polyethylene glycol.

6. The pharmaceutical composition according to claim 5, wherein polyethylene glycol has an average molecular weight of 3000–4000.

7. The pharmaceutical composition according to claim 1, wherein the pharmaceutical carrier comprises a mixture of sucrose and polyethylene glycol.

8. The pharmaceutical composition according to claim 7, wherein the mixing ratio, by weight, of polyethylene glycol and sucrose is from 1/10 to 10/1.

9. The pharmaceutical composition according to claim 7, wherein the mixing ratio by weight of polyethylene glycol and sucrose is 2/1.

10. The pharmaceutical composition according to claim 7, wherein the mixing ratio, by weight, of polyethylene glycol and sucrose is from 1.5/1 to 3/1.

11. The pharmaceutical composition according to claim 1, wherein the pharmaceutical carrier comprising polyoxyethylene sorbitan fatty acid ester.

12. The pharmaceutical composition according to claim 1, wherein the chondroitinase is chondroitinase ABC.

13. The pharmaceutical composition according to claim 1, wherein the specific activity of chondroitinase ABC is 300 U/mg protein or more.

14. The pharmaceutical composition according to claim 1 in the form of a freeze-dried preparation.

15. The pharmaceutical composition according to claim 1, wherein the amount of reducing impurities contained in 1 g of the pharmaceutical carrier is 0.09 mL or less as a titer by a titration method with 0.01 N ammonium ceric nitrate.

16. The pharmaceutical composition according to claim 1, wherein the peroxide content in the pharmaceutical carrier is 15 ppm or less.

17. The pharmaceutical composition according to claim 1, wherein the composition, in the form of a solution, retains at least about 60% of the enzyme activity of the chondroitinase, when stored for one month at 25° C relative to the enzyme activity before storage.

18. A method for the treatment of a mammal with herniation, which comprises injecting an effective amount of the pharmaceutical composition according to claim 1 into the intervertebral disc of the mammal.

19. A method for stabilizing the enzyme activity of chondroitinase which comprises, treating a pharmaceutical carrier having reducing impurities therein in an amount of greater than 0.4 mL as titer by a titration method with 0.01 N ammonium ceric nitrate, per 1 g of the carrier, with activated carbon to reduce the concentration of reducing impurities in 1 g of the carrier to a level of 0.4 mL or less, as a titer by a titration method with 0.01 N ammonium ceric nitrate, and mixing the so treated pharmaceutical carrier with chondroitinase to thereby form a stabilized chondroitinase composition wherein the enzyme activity of the stabilized chondroitinase composition, after storage at 25° C. in solution form for one month, is at least about 87% of the enzyme activity of the stabilized chondroitinase composition before storage.

20. The method according to claim 19 wherein the pharmaceutical carrier comprises polyethylene glycol, and said method further comprising freeze-drying the stabilized chondroitinase composition.

* * * * *